United States Patent [19]

Fukuda et al.

[11] 4,077,886
[45] Mar. 7, 1978

[54] CENTRIFUGAL LIQUID CHROMATOGRAPH

[75] Inventors: Tosao Fukuda, Kiryu; Hiroshi Takahashi, Ooarai, both of Japan

[73] Assignee: Japan Servo Co., Ltd., Tokyo, Japan

[21] Appl. No.: 652,846

[22] Filed: Jan. 27, 1976

[30] Foreign Application Priority Data

Jan. 28, 1975    Japan .................... 50/10957

[51] Int. Cl.² ............................................. B01D 15/08
[52] U.S. Cl. .............................. 210/198 C; 55/386
[58] Field of Search ............ 210/31 C, 198 C; 55/67, 55/197, 386

[56] References Cited

U.S. PATENT DOCUMENTS

| | | | |
|---|---|---|---|
| 3,078,647 | 2/1963 | Mosier | 55/197 |
| 3,417,548 | 12/1968 | Thompson | 55/67 |
| 3,527,350 | 9/1970 | Tuthill et al. | 210/198 C |
| 3,617,557 | 11/1971 | Giltrow | 210/198 P |

OTHER PUBLICATIONS

Continuous Surface Chromatography by Sussman et al. in Ind. Eng. Chem. Fundam., vol. 11, No. 2, 1972, pp. 181-185.

*Primary Examiner*—John Adee
*Attorney, Agent, or Firm*—Birch, Stewart, Kolasch and Birch

[57] ABSTRACT

A centrifugal liquid chromatograph, in which, in place of a prior art separating part in a liquid chromatograph, which portion is composed of a separating column and a feed pump, a pair of upper and lower horizontal discs are arranged vertically in spaced relation to each other, so that a separating medium may be filled in the gap defined therebetween, and the pair of discs are rotated, while a solvent as a mobile phase is being introduced through a central port provided in the upper disc into a space defined between the aforesaid pair of discs, whereby the mobile phase may make ingress into a stationary phase due to a centrifugal force, thereby achieving rapid separation of components from a sample, thus dispensing with a feed pump.

6 Claims, 15 Drawing Figures

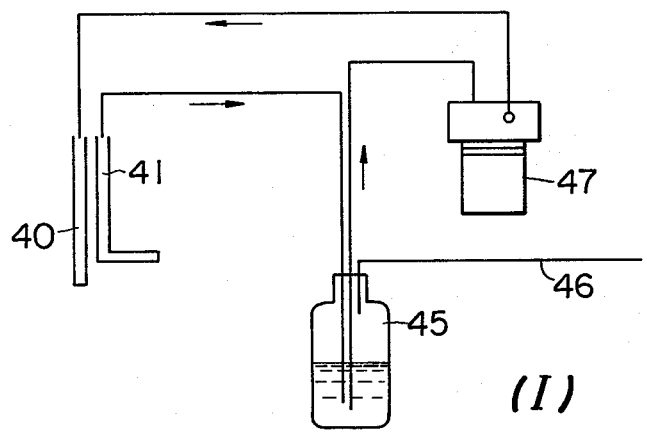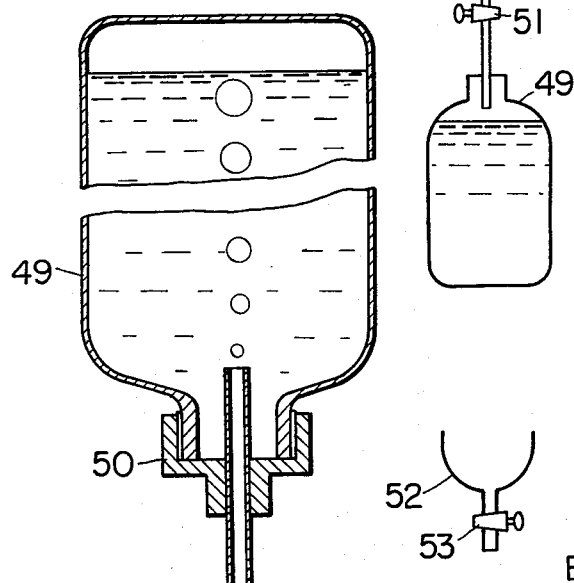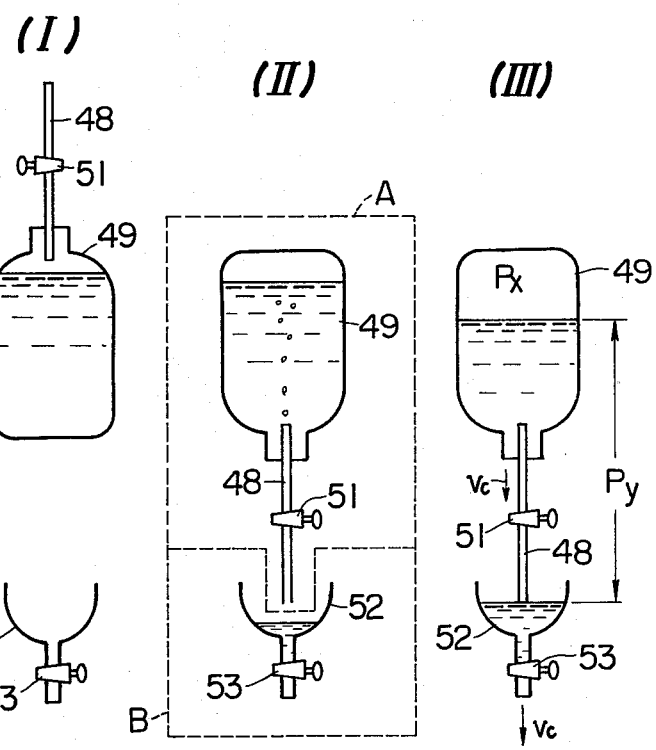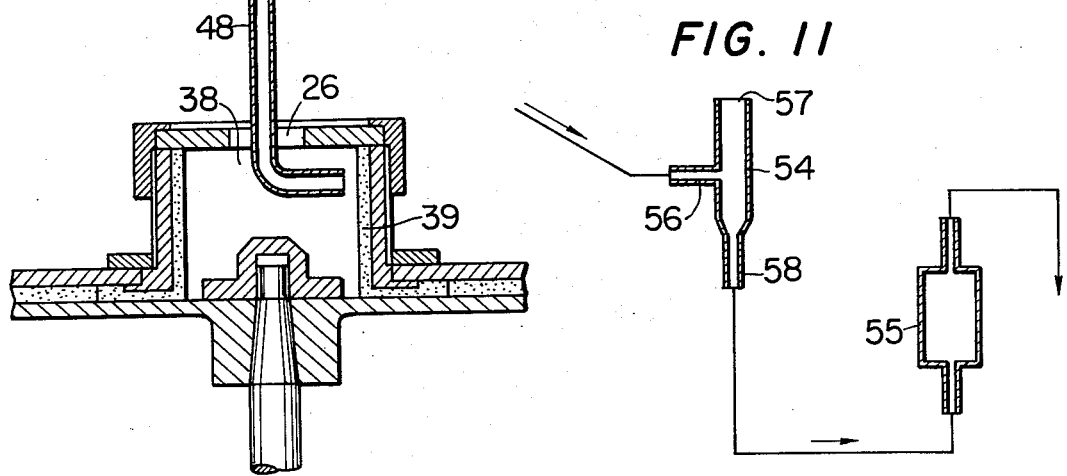

CENTRIFUGAL LIQUID CHROMATOGRAPH

BACKGROUND OF THE INVENTION

The present invention relates to a centrifugal liquid chromatograph, which separates components from a sample by utilizing centrifugal force.

A liquid chromatograph in general is composed of a combination of a separating part and a detecting part. In the separating part of a liquid chromatograph of the prior art, a system has been adopted, in which a solvent is charged as a mobile phase to a separating column filled with an absorbent as a stationary phase, and respective components are separated from one another due to the difference in interaction of respective components of a sample with the both stationary phase and mobile phase. Such a system however dictates the use of a feed pump for applying to the mobile phase a pressure sufficiently high to move the mobile phase into the separating column. It is desirable that such a feed pump be employable for an organic solvent, strong acid solution or alkaline solution. However, a pump of such a universal type is hardly obtainable from the viewpoint of materials.

SUMMARY OF THE INVENTION

It is accordingly an object of the present invention to provide a centrifugal liquid chromatograph, in which, in place of the prior art separating part in a liquid chromatograph, which portion is composed of a separating column and a feed pump, a pair of discs are rotatably arranged in vertically spaced relationship, and a separating medium is filled in the space defined therebetween, said pair of discs being rotated so that a mobile phase may make ingress into the stationary phase due to centrifugal force.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within ghe spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

FIG. 8 shows a still further embodiment of the present invention, wherein another type, automatic developer supply mechanism is provided;

FIG. 9 shows a still further embodiment of the present invention, wherein still another type automatic developer supply mechanism is provided;

FIG. 10 illustrates the modes of operation of the device shown in FIG. 9; and

FIG. 11 shows an embodiment of the present invention, wherein a defoamer is provided.

DESCRIPTION OF PREFERRED EMBODIMENTS

A description will now be given directed to the embodiments of the present invention, with reference to the accompanying drawings.

Figure 1:
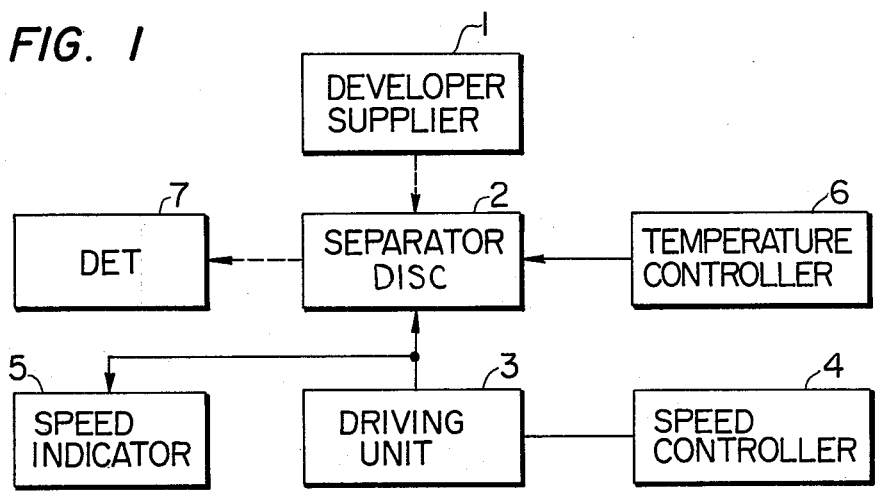
FIG. 1 is a block diagram showing the outline of the construction of the present invention.

FIG. 1 is a block diagram showing the outline of the construction of the present invention. Shown at 1 is a developer supplier, which is a small separating funnel having a decreasing diameter in the direction of a liquid outlet port, and to which an automatic syringe or other liquid distributor may be connected. Designated 2 is a separator disc which is composed of a pair of upper and lower horizontal discs. Shown at 3 is a drive unit, which is a drive mechanism for transmitting a drive force to the separator disc 2 by way of an electric motor, gears a belt engaged with the separator disc 2 directly. Shown at 4 is a speed controller, which consists of a circuit for electrically controlling the r.p.m. of the drive unit 3, the speed controller being provided for the purposes of; causing a mobile phase to make ingress into the separator disc 2; accommodating the moving rate of a developer to the nature of a sample used; filling a separating medium in a gap between the pair of upper and lower discs of the separator disc 2; and adhering a sample to the separator disc 2. Designated 5 is a speed indicator, which electrically or mechanically detects the r.p.m. of the separator disc 2 and indicates the r.p.m. thus detected. Shown at 6 is a temperature controller which consists of a circuit for adjusting a temperature in the separator disc 2. Shown at 7 is a detector. In case components separated from a sample provides a distinct color band in the separator disc 2, one can watch it in place of the detector 7 (In such a case, the upper disc should be made of a transparent material). For the sake of precision, there may be used a variety of spot detectors for use in paper chromatography or thin layer chromatography. In case it is desired to collect an effluent discharged from the separator disc 2, a variety of detectors adapted for use in the column chromatography may be used.

Figure 2:
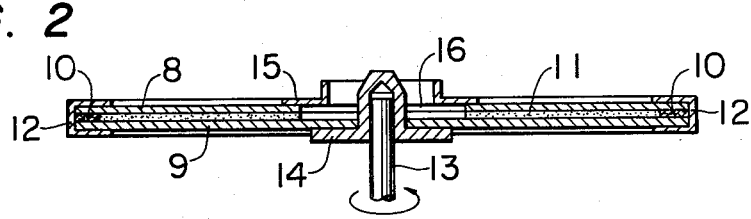
FIG. 2 is a longitudinal cross sectional view of a separator disc according to one embodiment of the present invention.

FIG. 2 is a longitudinal cross sectional view showing an embodiment of the separator disc 2. Shown at 8 is a horizontal upper disc, and at 9 a horizontal lower disc, the upper and lower discs being spaced apart vertically a given distance from each other by means of a spacer 10. The spacer 10 serves to adjust the thickness of a separating medium as well as prevent escape of the separating media from the outer circumferential portion of the separator disc. The spacer 10 may be made of a sheet of filter cloth, filter paper or felt, or other porous thin sheets. Shown at 11 is a separating medium which is filled in a gap between the upper disc 8 and the lower disc 9. Shown at 12 is a supporting member for supporting the circumferential portions of both discs, at 13 a rotary shaft, and at 14 lower disc supporting member, which serves for transmitting the torque of the rotary shaft 13 to the upper and lower discs 8 and 9. Designated 15 is a holder for use with the upper disc 8. Shown at 16 is a inlet port provided in the central portion of the upper disc 8, through which a sample or a developer medium is fed into the separator disc.

In order to charge the separating media 11 into the gap between the upper disc 8 and the lower disc 9, a given quantity of separating medium prepared in paste state with a proper solvent is introduced little, by little from the beginning of rotation through the inlet port 16, while the upper and lower discs 8 and 9 are being rotated at a low speed of 30 to 300 r.p.m., then gradually to an increased r.p.m., and ultimately to a speed of 1000 to 3000 r.p.m., whereby the separating media fills the gap between the two discs due to a centrifugal force.

Upon feeding of a sample to the separator disc, a sample dissolved with a proper solvent or a separating medium having a sample adsorbed thereto is precisely weighed. If the sample is a liquid, a sample in the form of a solution is injected into the separator disc by means such as a syringe. If the sample is a solid, a sample in the form of a powder is added little by little, whereby it is charged into the separator disc due to centrifugal force.

With the arrangement of FIG. 1, if the separator disc 2 charged with the separating media containing a sample is rotated by means of the drive unit 3 while a developer is being fed thereto from the developer supplier 1, then the developer is moved, due to a centrifugal force, radially outwards in the gap between the two discs to make ingress into the separating media 11, and respective components contained in the sample are separated in the form of a concentric ring, with the movement of the developer. Various liquid separating media for use in chromatography, which ranges from 100 to 400 meshes in grain size, are applicable so long as a thickness of the spacer 10 is properly selected. By selecting a separating medium, a developer and the r.p.m. of the separator disc properly according to the nature of a sample used, the rapid and simple separation of components from the sample result. In case such components can be colored within the separator disc, qualitative and quantitative analyses for every component are visually achieved, and on the other hand, in case such components are of a non-colored matter, then the qualitative and quantitative analyses are achieved either by removing the upper disc 8 after the termination of the intended rotation of the separator disc and by spraying the components with a type of color former which can be used in thin layer chromatography, or by using various types of spot detectors. Otherwise, adsorbed components may be collected for separation of the pure components. As an alternative, a liquid chromatograph detector of a general type is provided so as to detect respective components discharged from the separator disc 2, thereby conducting continuously qualitative and quantitative analyses and separation.

Figure 3A:
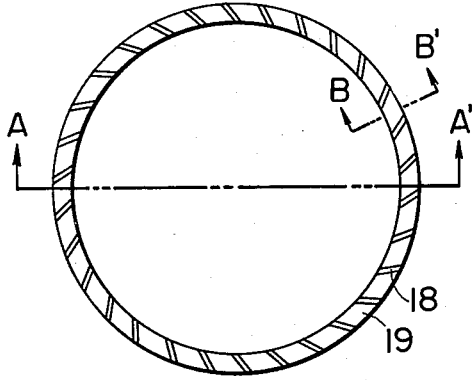
FIG. 3a-3c is a view showing an embodiment of a spacer which is used in the present invention.
Figure 3B:
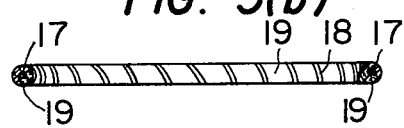
Figure 3C:

FIG. 3 shows an embodiment of the spacer 10 which is used in the present invention, wherein (a) is a plan view, (b) is a cross sectional view taken along the line A—A', and (c) is a cross sectional view taken along the line B—B'. The requirements for the spacer used in the separator disc 2 are such that only a developer or components separated from a sample are allowed to pass therethrough but the separating medium is not; there is no possibility of a developer and separating media leaking from an interstices between the spacer and respective discs 8 and 9; and the spacer should maintain a ring or doughnut shape, without being deformed through a repeated service of the chromatographic device.

The spacer of FIG. 3 is of a construction that satisfies the above requirements. The spacer consists of a ring-shaped, rigid core wire, around which a rigid wire of a considerably small gage is wound in a spiral form substantially at a constant pitch, with a porous material wound around the core wire in a manner to fill the gaps between the adjoining wires of small gage, which appear on the outer surface of the core wire.

In FIG. 3, shown at 17 is a ring-shaped core wire of stainless steel, at 18 a stainless steel wire of a considerably small gage which is wound around the core wire 17 in a spiral form substantially at a constant pitch, and at 19 a tape of glass fiber wound around the core wire 17 in a manner to fill in the gaps between the adjoining wires of small gage.

It is preferable to use as a core wire 17 a wire of stainless steel whose diameter is sufficiently large so that such a wire will not be deformed due to a centrifugal force. Stated otherwise, by using a core wire of a small gage, there may be obtained a spacer of almost the same performance as that of a spacer made of a porous material only. The length of fine wire 18 spirally wound around the core wire 17 serves for reinforcing the core wire 17 as well as adjusting a thickness of the spacer and acts to prevent the separation of the tape of glass fiber 19 off the outer surface of the core wire 17.

In this manner, there is obtained a spacer, whose ring-shaped core wire 17 maintains the freedom of deformation due to movement of a developer or a centrifugal force, whose thickness remains unchanged through the repetitive service of the device because of the wire 18 of a considerably fine gage wound around the core wire 17, and which is less costly to manufacture.

Figure 4A:
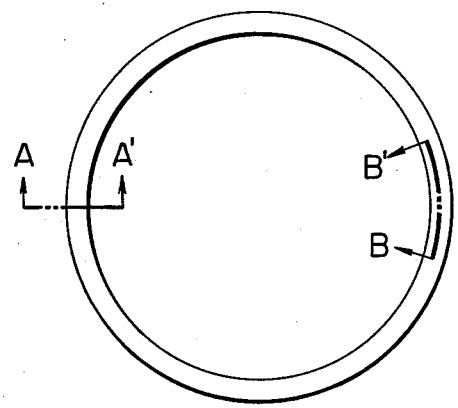
FIG. 4a-4c illustrates another embodiment of a spacer.
Figure 4B:
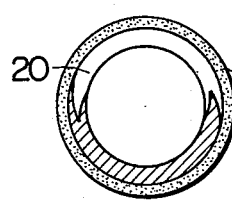
Figure 4C:
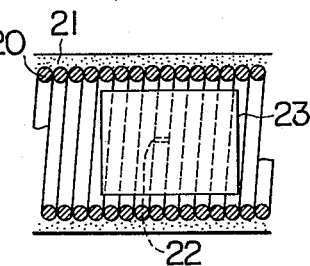

FIG. 4 shows another embodiment of the spacer which is used in the present invention, wherein (a) is a plan view, (b) is a cross-sectional view taken along the line A—A', and (c) is a cross-sectional view taken along the line B—B'. The spacer in this embodiment consists of a ring-shaped core which is obtained by coiling a rigid wire of a considerably small gage in a spiral form in intimately contacting relationship but in a single layer, so as to give a tubular shape and forming the coil thus prepared into a ring shape, with a porous material covering the outer surface of the core, thus providing a function of a spacer.

In FIG. 4, element 20 is a ring-shaped core which is obtained by coiling a length of steel wire of a considerably small gage in a spiral form in intimately contacting relationship or tightly in a single layer into a tubular shape and forming the coil thus prepared into a ring shape, and element 21 a tube of a porous material, such as cotton-make knit tube, covering the outer surface of the core coil 20. In order to prepare a coil ring, a length of coil subjected to quenching is cut into a piece of a desired length, and the coil of a desired length is butt-welded at the opposite ends, or a plug 23 is inserted in the abutting portion 22 of the coil 20, as seen in FIG. 4 (c). In place of the aforedescribed procedures wherein the core ring is first shaped into a ring and then covered with a porous material, the coil is provided with a cotton-make knit tube and then the coil is shaped into a ring, with the plug 23 inserted therein, and finally the opposite ends of the knit tube are seamed together.

Figure 5:
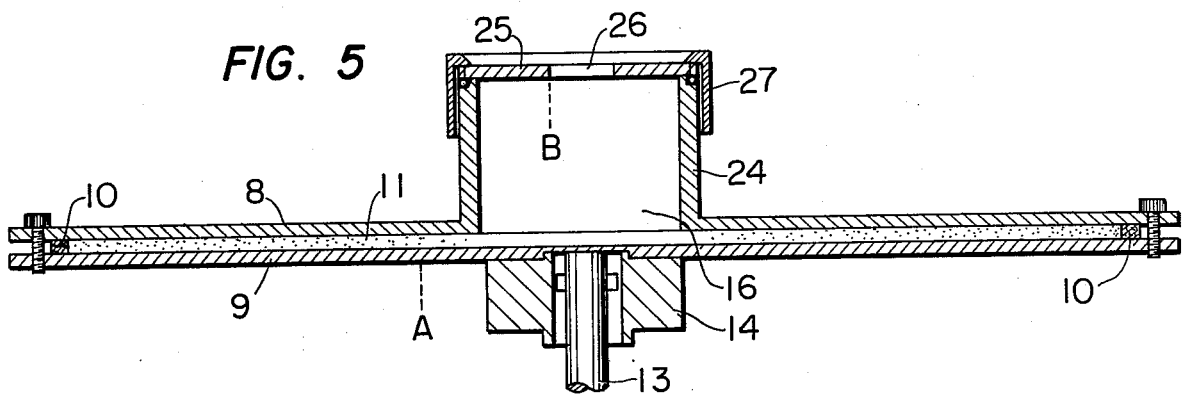
FIG. 5 is a longitudinal cross sectional view showing, in detail, the construction of a part in the vicinity of a solvent inlet port provided in the central portion of an upper separator disc, according to an embodiment of the present invention.

FIG. 5 is a longitudinal cross sectional view showing in detail the construction of portions of the device of the present invention in the vicinity of the solvent inlet port 16 provided in the central portion of the upper disc 8. The developer is fed through the solvent inlet port 16 and received in a space defined by the solvent inlet port 16, lower disc 9 and inner periphery of the separating media. In case the volume in said space is not large enough, as compared with a quantity of developer being discharged from the peripheral portion of the separator disc, unless the developer is continuously fed in a given quantity by using, for example, a constant discharge feed pump, then movement of the developer becomes irregular, resulting in the failure to effect reproducible separation. Use of a constant discharge feed pump, however, is incompatible with the characteristics of the present invention.

For this reason, according to the present invention, there are provided a cylinder wall 24 projecting upwards from the circumference of the solvent inlet port 16 and rigidly secured to the upper disc 8, and a space defined by the inner wall surface of the cylinder 24, lower disc 9 and inner peripheral surface (shown as at A) of the separating media, the aforesaid space serving as a developer reservoir, for storing therein a developer necessary for the development for a given duration. In FIG. 5, shown at 24 is a cylinder wall, which is formed integrally with the upper disc 8 and projects upwards of the upper disc 8 in a manner to enclose the solvent inlet port 16. Shown at 25 is a window which is made of a transparent plate and constitutes the upper end of the cylinder wall 24, and at 26 is a developer inlet port provided in the window 25. Designated at 27 is a holder for attaching the window 25 to the cylinder wall 24. When the r.p.m. of the upper and lower discs 8 and 9 is increased to more than a given value, the developer being fed through the developer inlet port 26 to the cylinder wall goes towards the outer periphery of the separating media 11 while forming a developer cylinder having the outer peripheral surface i.e., the inner peripheral surface shown as at A in FIG. 5, of the separating media 11.

This movement of the developer allows the feeding of the developer to the separator disc at a time, until the inner peripheral surface of the developer cylinder becomes in alignment with the circumference shown as at B, of the developer inlet port 26. If the r.p.m. of the upper and lower discs 8 and 9 is constant, even if there arises fluctuation in quantity of developer being fed, or there arises a positional change in the inner peripheral surface of the developer cylinder, with the progress of the developing movement of the developer. As long as the inner peripheral surface of the developer cylinder assumes a position which falls in a range from the surface B to the surface A shown in FIG. 5, then a developer pressure which is to be applied to the inner periphery, i.e. the surface A, of the separating media will remain unchanged, similarly as the rate of movement of the developer, thus providing a constant separation efficiency. An increase in vertical length of the cylinder wall 24 for increasing the capacity thereof does not adversely affect the performance of the device serving as a liquid chromatograph, as long as the cylinder wall 24 is so constructed that its vertical wall extends exactly at a right angle to the upper disc 8.

Thus, the developer reservoir affords a spatial volume much larger than the quantity of developer being discharged from the outer peripheral portion of the separating media, so that the reproducibility required is sustained, dispensing with an expensive, constant discharge feed pump, even in the case where the developer is fed at a desired interval of time by means of a dropping funnel. Thus, the cylinder wall 24 is useful even in the case where the separating media 11 is filled in the gap between the upper disc 8 and the lower disc 9.

Figure 6:
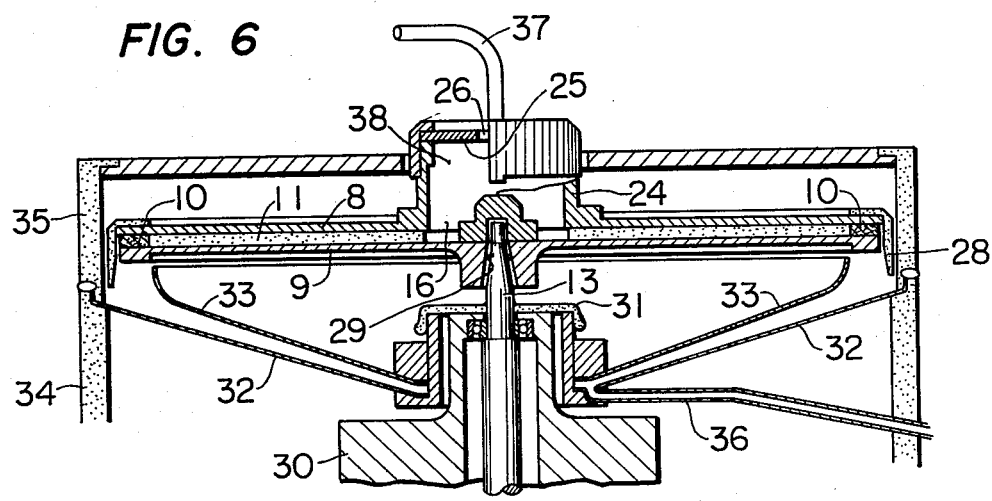
FIG. 6 is a longitudinal cross sectional view of the construction of the present invention according to another embodiment, wherein an interrupter, liquid guide and deflector are provided.

FIG. 6 is a longitudinal cross sectional view of the device wherein the utilization of an interrupter, a liquid guide and a reflector provide an increased separation efficiency. Shown at 28 is an interrupter fastened by means of bolts to the upper disc 8. The interrupter acts to aggregate the developer and components which have been separated and discharged as fine particles through perforations of the spacer 10, with the rotation of the upper and lower discs 8 and 9, as well as to guide a direction of movement of the aggregate. The interrupter 28, in this embodiment, is fastened by means of bolts to the outer circumferential portion of the upper disc 8 in a manner to be inclined with respect to the outer periphery of the disc. As an alternative, the interrupter may be disposed at a right angle to the outer periphery of the upper disc 8, or may be formed integrally with the upper disc 8. Shown at 13 is a rotary shaft, which is removably fitted at its top end in a circular groove provided in the lower disc 9 and which is adapted to rotate the upper and lower disc 8 and 9 with the aid of pins 29. Designated 30 is a bearing portion, in which the rotary shaft 13 is journaled. By removing the holder 31, the liquid guide 32 and reflector are removed from the device. The liquid guide 32 is of an inverted truncated conical shape and made of a thin plate of synthetic resin. The liquid guide 32 is removable secured through the intermediary of the holder 31 to the outer periphery of the bearing portion 30 and acts to receive the developer and components separated from a sample which are discharged from the outer peripheral portion of the separating media 11. The outer circumference of the liquid guide 32 is inserted and held in the joint portion of a casing 34 of the separating part and a casing cover 35, so that the liquid guide 32 may be removed with ease from the casing 34, with the casing cover 35 removed. The reflector 33 is disposed above the liquid guide 32 in facing relation thereto, with a small space left therebetween, and has a cylindrical center portion which is removably secured to the outer periphery of the central cylindrical portion of the liquid guide 32.

The components separated from a sample which are discharged simultaneously from respective peripheral portions of the upper and lower discs 8 and 9 will be delivered onto the inclined surface of the liquid guide 32 at a given rate commensurate to the r.p.m. of the upper and lower discs 8 and 9. At this time, the spatter of liquid from the inclined surface of the liquid guide 32 will impinge on the undersurface of the reflector 33 and then returned onto the liquid guide 32.

The inclined surface of the liquid guide 32 is small in gradient, such that all of the components separated from a sample will be delivered to the same circumference of the inclined surface of the liquid guide 32, and directed at the same rate to the liquid outlet port 36. In short, there is no possibility that components separated from a sample which have been previously discharged onto the inclined surface of the liquid guide 32 are mixed with the components subsequently discharged onto the inclined surface of the liquid guide 32. Furthermore, the reflector 33 and liquid guide 32 are removed readily from the bearing portion 30 by removing the casing cover 35 from the casing 34, then the upper and lower discs 8 and 9 from the rotary shaft 13, and then the holder 31 therefrom, so that cleaning of the inclined surface of the liquid guide 32, reflector 33 and other portions is conducted with ease for removal of residual sample used in the preceding measurement. This eliminates the possibility that components of a subsequent sample will be contaminated with a sample used in a preceding measurement, with the result of improved separation efficiency. Shown at 37 is a developer supply pipe which is supported by supporting means (not shown) and used for feeding the developer to a space 38 for use in storing developer.

Figure 7:
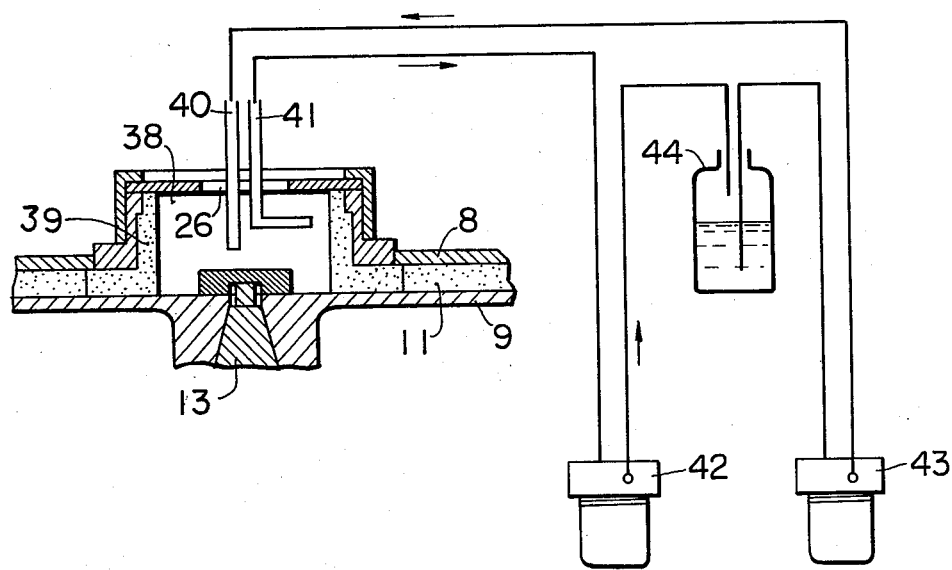
FIG. 7 shows a further embodiment of the present invention, wherein an automatic developer supply mechanism is provided.

FIG. 7 shows an embodiment of a device equipped with an automatic developer supply system. As is apparent from the foregoing, the centrifugal liquid chromatograph of the present invention is characterized in that neither pressure pump nor other liquid supply pump is used, unlike the liquid chromatograph of the prior art. However, a problem arises in the centrifugal liquid chromatograph of this type, in that a quantity of developer flowing through the separator disc is subjected to the limitation arising from the centrifugal force and the filling density of the separating media, and therefore, if a quantity of developer being fed to the separator disc is adjusted, the flow rate of the developer running through the separator disc would not necessarily be correspondingly adjusted.

Stated otherwise, if a quantity of developer being fed to the separator disc is maintained below the limit of flow rate due to the centrifugal force and filling density of the separating media, the quantity of developer being discharged from the separator disc would be equal to the quantity of developer fed. In such a case, air would be included in a layer of separating media, and the developer would be moved as fine particles among the particles of separating media therethrough. This incurs a delicate change in the rate of movement of components of a sample from the developer to the separating media, and vice versa, resulting in a lowered separation efficiency.

On the contrary, should a quantity of developer being fed be set to more than the limit of flow rate, then the developer would eventually overflow from the space 38 used for storing developer, causing another problem.

It is thus ideal in centrifugal liquid chromatograph that the quantity of developer being fed be adjusted to be equal to the limit of the flow rate. However, such an adjustment is rather difficult.

FIG. 7 shows the device equipped with an automatic developer supply mechanism. Shown at 39 is a developer cylinder which is to be formed in the space 38 for storing developer, for the period of time in which centrifugal force is being created due to the rotation of a separator disc. Shown at 40 is a developer supply pipe, which is removably arranged, with its one end open to a space 38 for storing developer and with its other end connected to a developer supply pump 43. Designated 41 is a developer suction pipe which is removably arranged, with its one end open to a given position at the inner diameter of the developer cylinder 39 and with the other end connected to a developer suction pump 42. Shown at 44 is a developer reservoir, which is connected to the developer suction pump 42 as well as the developer supply pump 43.

If the upper and lower discs 8 and 9 are rotated and the developer is fed from the developer supply pipe 40, and if the quantity of developer being introduced is no less than the limit of the flow rate, then the excessive developer will reside in the space 38 for storing developer, forming the developer cylinder 39 due to a centrifugal force. With a lapse of time, the wall thickness of the developer cylinder 39 will increase, and eventually the developer will overflow from the developer inlet port 26. To avoid the overflow of developer, the developer suction pump 42 is turned on, so that when the inner peripheral surface of the developer cylinder 39 reaches the open end of the developer suction pipe 41, the excessive developer will be pumped up, whereby the inner periphery of the developer cylinder 39 assumes a constant position in the space 38 all the times, while the excessive developer is recirculated through the developer supply line for re-use.

FIG. 8 illustrates another embodiment of the device equipped with an automatic liquid supply mechanism. In FIG. 8, shown at 45 is a developer reservoir, at 46 a pressure reducing line connected to the developer reservoir, and at 47 a developer supply pump. The developer is circulated in the direction of arrows through the suction pipe 41, reservoir 45, supply pump 47 and supply pipe 40. In this case, the pressure reduction in the pressure reducing line is of a level, at which an excessive developer can be pumped up. The developer supply pump 47 should not always be an electrically driven pump. In place of the developer supply pump 47, a funnel with a plug may be used by properly selecting a position of installation of the developer reservoir 45. If automatic supply interrupting means interlocking with the suction pump is attached to the developer supply line, so as to interrupt circulation of the developer through the supply line, simultaneously with the stopping of the pumping action, there results improved reliability of the device itself.

FIG. 9 shows a still further embodiment of the device equipped with an automatic developer supply mechanism. Shown at 48 is an air-inlet pipe, at 49 a developer reservoir, and at 50 a cap for the developer reservoir, which is fitted in a light-tight manner over the lower opening of the developer reservoir 49 as well as the air-inlet pipe 48 extending to the interior of the reservoir 49. Provided midway along the air-inlet pipe 48 is a plug for opening or closing a liquid passage, which will be referred to in conjunction with FIG. 10. The liquid supply mechanism consisting of the pipe 48, reservoir 49 and cap 50 is removably retained above the upper and lower discs 8 and 9.

The principle of the automatic developer supply mechanism shown in FIG. 9 will be described in detail with reference to FIG. 10. In FIG. 10, shown at 49 is a developer reservoir, to which is attached an air-inlet pipe 48 having a plug 51. Designated 52 is a funnel with a plug 53. If the developer reservoir 49 filled with a developer in a normal position I is set in an inverted position (II), and the plug 51 is opened, then air in the reservoir 49 will be expanded into a pressure-reduced condition and the developer in the reservoir 49 is transferred by its own weight into the funnel 52 with a plug. In this case, if the inner diameter of the air-inlet pipe 48 is less than a certain value, then the flow of the developer to the funnel will be interrupted when the sum of pressure of air within the reservoir and a static pressure of the residual developer becomes equal to atmospheric pressure, and resultantly an equilibrium in pressure is established. In case the air-inlet pipe 48 has an inner diameter resonably larger than a certain value, the equilibrium in pressure will be broken before long, and the air is resultantly introduced through the air-inlet pipe 48 into the developer reservoir 49, thus reducing a pressure in the reservoir, whereby the developer is again caused to flow into the funnel, until an equilibrium in pressure is re-established. The equilibrium in pressure however does not last for a long period of time, and introduction of air into the reservoir and the outflow of the developer therefrom are repeated periodically until the level of the developer in the funnel 52 reaches the lower open end of the air-inlet pipe 48. A stable equilibrium in pressure is not established until the level of developer within the funnel is raised to the lower open end of the pipe 48 so that admission of air into the reservoir 49 is no longer allowed.

Description will go on, on the assumption that the air-inlet pipe 48 having a proper inner diameter is used; the level of the developer in the funnel is raised to the lower open end of the pipe; and a stable equilibrium in pressure is established. Under such a situation, if the plug 53 of the funnel 52 is turned open (the situation III), then the developer within the funnel 52 is discharged, and in turn air is introduced into the reservoir 49, as the developer is being discharged from the funnel, so as to prevent the lowering of the level of the developer in the funnel 52, whereby the developer is fed to the funnel 52 in a quantity commensurate to a quantity of developer being discharged from the funnel. Thus, the developer is continuously discharged in a given quantity from the funnel while the developer within the funnel is maintained on a level with the lower end of the air-inlet pipe 48.

The funnel 52 with a plug shown in FIG. 10 is quite the same in function as the separator plate having a space 38 for storing developer shown in FIG. 9. In more detail, a quantity of developer being discharged from the funnel 52 in FIG. 10 corresponds to a quantity of developer being discharged from the separator plate in FIG. 9, while the level of developer within the funnel 52 in the former corresponds to the inner periphery of the developer cylinder 39 which is to be formed in the space 38 for storing developer in the separator plate in the latter. In the embodiment of FIG. 9, wherein the developer reservoir 49 and air-inlet pipe 48 are arranged above the separator plate, if the developer is charged into the space 38 for storing developer prior to separation and the separator plate is rotated, then the developer will be adhered, in the form of a cylinder, to the cylinder wall of the space for developer storage 38. At this stage, a plug (not shown) attached to the air-inlet pipe 48 is opened and the developer is fed to the separator plate under the same condition as in FIG. 10 (II). In this embodiment, if an inner diameter of the pipe 38 and other factors are adjusted in a manner that a quantity of developer being fed from the air-inlet pipe per unit time is greater than the limit of flow rate of the developer being discharged from the separator disc, then the developer will be fed into the separator disc, while maintaining the condition in a manner that the quantity of developer being introduced is equal to the quantity of developer being discharged, and thus maintaining constant the position of the inner peripheral surface of the developer cylinder 39 relative to the open end of the inlet pipe 38 (in FIG. 9).

In the embodiments of FIGS. 9 and 10, the air-inlet pipe 48 is used as a developer supply pipe as well. Both pipes however may be provided separately. Only a single developer reservoir is used in the embodiments shown, but a plurality of reservoirs interconnected by means of pipes with a plug may be used, so that solvent of different types may be charged in respective reservoirs.

According to the arrangement of FIG. 9, which comprises an atmospheric pressure equilibrium type, automatic developer supply mechanism equipped with an air-intake pipe for maintaining constant the inner diameter of the developer cylinder, which is to be formed in the developer storage portion in the separator disc during the separation process, there is established the condition that the quantity of developer being fed to the separator disc, the quantity of developer being discharged from the separator disc and the quantity of developer to be discharged from separator disc are made equal to one another. Furthermore, the developer is automatically supplied to the separator disc by the arrangement of the device having a simple construction. The arrangement of FIG. 9 therefore is particularly useful as a laboratory chromatograph in which a quantity of sample being processed is not so excessive.

FIG. 11 shows an embodiment of the construction, in which there is provided a defoamer for removing air bubbles contained in the liquid discharged from the separator disc. The defoamer 54 is disposed on the upstream side of the detector 55, as viewed from the separator plate and has an inlet pipe 56 connected to the liquid outlet pipe 36 (in FIG. 6), an air outlet pipe 57 and a liquid outlet pipe 58 connected to the detector 55. The effluent, which contains air bubbles and comes through the liquid outlet pipe 36 in the separating portion, is separated from air bubbles when dropping from the port open to the wall of the thick tubular defoamer, and in turn air bubbles will be discharged through the air port 57 to the outside, while the effluent thus defoamed is introduced into the detector 55.

In case the defoamer 54, is disposed between the separator plate and the detector 55 as in the embodiment of FIG. 11, a conventional detector for use in the liquid chromatograph of the prior art can be used as it is for the centrifugal liquid chromatograph, without a risk of trouble. The defoamer 54 is not limited to the arrangement shown in FIG. 11 but may be modified into various configurations, so far as a proper air outlet port is provided.

As is apparent from the foregoing, by the provision of the defoamer in the upstream side of the detector, various detectors may be used, as they are, without being remolded or without using an electric circuit for removing air bubbles, such as a ultra-violet absorption detector, a fluorescence photometer, a radioactivity detector, a polarograph detector, a differential refractometer or a conductivity meter, all of which have been developed for use in the column type liquid chromatograph of the prior art.

In the centrifugal liquid chromatograph according to the present invention, the separator disc consisting of a pair of discs and a spacer is used, in place of a column in the liquid chromatograph of the prior art, and a drive unit adjustable in its r.p.m. is used in place of a constant pressure pump in the prior device. The separator disc and drive unit in combination fulfil the function of the chromatograph, thereby achieving analysis and separation, rapidly and with ease.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A centrifugal liquid chromatograph comprising;
separating means consisting of a pair of upper and lower horizontal discs which are vertically arranged in spaced-apart relationship with respect to each other, and a porous spacer disposed between said pair of discs along the circumference thereof, said separating means having a space defined between said pair of discs and filled with a separating medium, said upper disc having a central inlet port, through which a sample and a developer are to be fed to said separating means, said porous spacer consisting of a rigid core wire having a ring shape and a coil of rigid wire of a considerably small gauge wound around said rigid core wire in a spiral form at substantially a constant pitch and a tape of porous material closely adhered to the coil of rigid wire of considerably small gauge in a manner to fill the respective gaps between the adjoining wires of a considerably small gauge;
a drive unit for rotating said separating means in a manner to permit adjustment of the r.p.m. thereof, and for forcing components separated from a sample towards the circumferential portion of said separating means due to centrifugal force; and
detecting means for receiving the sample forced out from the outer circumferential portion of said separating means and detecting components separated from the sample.

2. A centrifugal liquid chromatograph as defined in claim 1, wherein a cylindrical wall is attached to said upper disc, said cylindrical wall projecting upwards but outwards from the circumferential portion of the central inlet port provided in said upper disc, and having an internal space serving as a reservoir for storing the developer necessary for development of the sample for a given period of time.

3. A centrifugal liquid chromatograph as defined in claim 1, wherein said separating means is removably secured through the intermediary of the lower disc thereof to a rotary shaft of said drive unit, and a truncated conical shaped liquid guide is removably secured to the outer periphery of a bearing for said rotary shaft, said conical liquid guide being located below said separating means and being adapted to receive therein the developer as well as components of the sample which are discharged from the outer circumferential portion of said separating means.

4. A centrifugal liquid chromatograph as defined in claim 3, wherein a reflector is removably mounted on the outer periphery of a bearing for said rotary shaft, said reflector having an inclined surface and being disposed above the inclined surface of said conical shaped liquid guide, with its inclined surface facing the inclined surface of the liquid guide at a small spacing therefrom.

5. A centrifugal liquid chromatograph as defined in claim 3, wherein there is provided an automatic developer supply mechanism having a developer suction pipe, said developer suction pipe having one end open in a given position on an inner diameter of a developer cylinder which is to be formed by the developer in the developer charging portion according to the rotation of said separating means, and said automatic developer supply mechanism feeding circulatively excessive developer through a developer supply line into said developer charging portion, said excessive developer being pumped up through said suction pipe.

6. A centrifugal liquid chromatograph as defined in claim 3, wherein there are provided a defoamer and a detector disposed on the downstream side of said defoamer as viewed from the separating means, said defoamer removing air bubbles contained in the developer as well as components separated from the sample which have been forced out from said separating means.

* * * * *